United States Patent [19]
Larsen et al.

[11] Patent Number: 5,968,011
[45] Date of Patent: Oct. 19, 1999

[54] SUBCUTANEOUS INJECTION SET

[75] Inventors: Bjorn Gullak Larsen; Orla Mathiasen; Lars Bjarne Frederiksen; Marc Delzac, all of Roskilde; Claude Teisen-Simony, Frederiksberg, all of Denmark

[73] Assignee: Maersk Medical A/S, Lynze, Denmark

[21] Appl. No.: 08/879,525

[22] Filed: Jun. 20, 1997

[51] Int. Cl.[6] .......................... A61M 11/00; A61M 5/178; A61M 25/00

[52] U.S. Cl. .................. 604/93; 604/167; 604/164; 604/283

[58] Field of Search .................... 604/93, 30, 32, 604/164, 167, 169, 246, 247, 248, 280, 283; 137/625.46; 251/208

[56] References Cited

U.S. PATENT DOCUMENTS

| | | |
|---|---|---|
| 4,755,173 | 7/1988 | Konopka et al. ................. 604/167 |
| 4,966,588 | 10/1990 | Rayman et al. . |
| 5,176,662 | 1/1993 | Bartholomew et al. ............ 604/283 |
| 5,207,641 | 5/1993 | Allton ............................. 604/32 |
| 5,522,803 | 6/1996 | Teissen-Simony . |
| 5,545,143 | 8/1996 | Fischell . |

*Primary Examiner*—Wynn Wood Coggins
*Assistant Examiner*—Michael J Hayes
*Attorney, Agent, or Firm*—Brinks Hofer Gilson & Lione; William A. Webb; John G. Rauch

[57] ABSTRACT

A subcutaneous injection set for administering a medication or a therapeutic fluid to a patient is disclosed. The injection set comprises a base element having a hub with a top and a bottom and an outer surface extending between said top and said bottom, a cavity within said hub and an entry lumen extending from said outer surface to said cavity. A top element is mounted on said base element to be rotatable about an axis through said hub and having a flange with an inner surface mating with said outer surface of said hub in the area around the entry lumen, said flange having an aperture extending between said inner surface and an outer surface, which aperture in one position of the top element in relation to the base element is aligned with said entry lumen of said hub and said flange in a further rotated position of the top element in relation to the base element covers said entry lumen in said hub. A cannula is mounted in and extending from said hub of said base element, said cannula having a lumen therethrough, said lumen communicating with the entry lumen of the central hub through said cavity. Connector means for administering a fluid to said opening in said flange of said top element are provided.

30 Claims, 18 Drawing Sheets

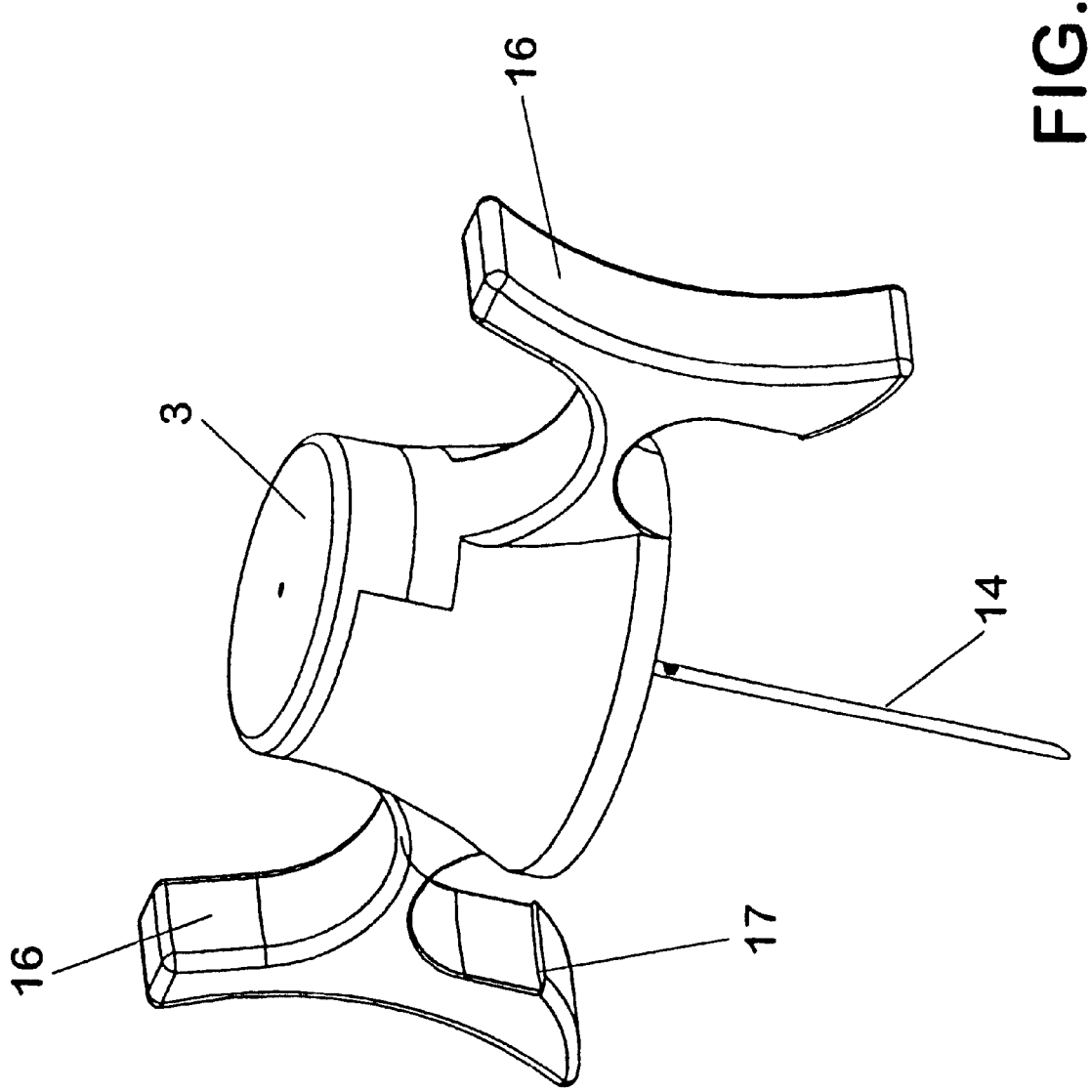

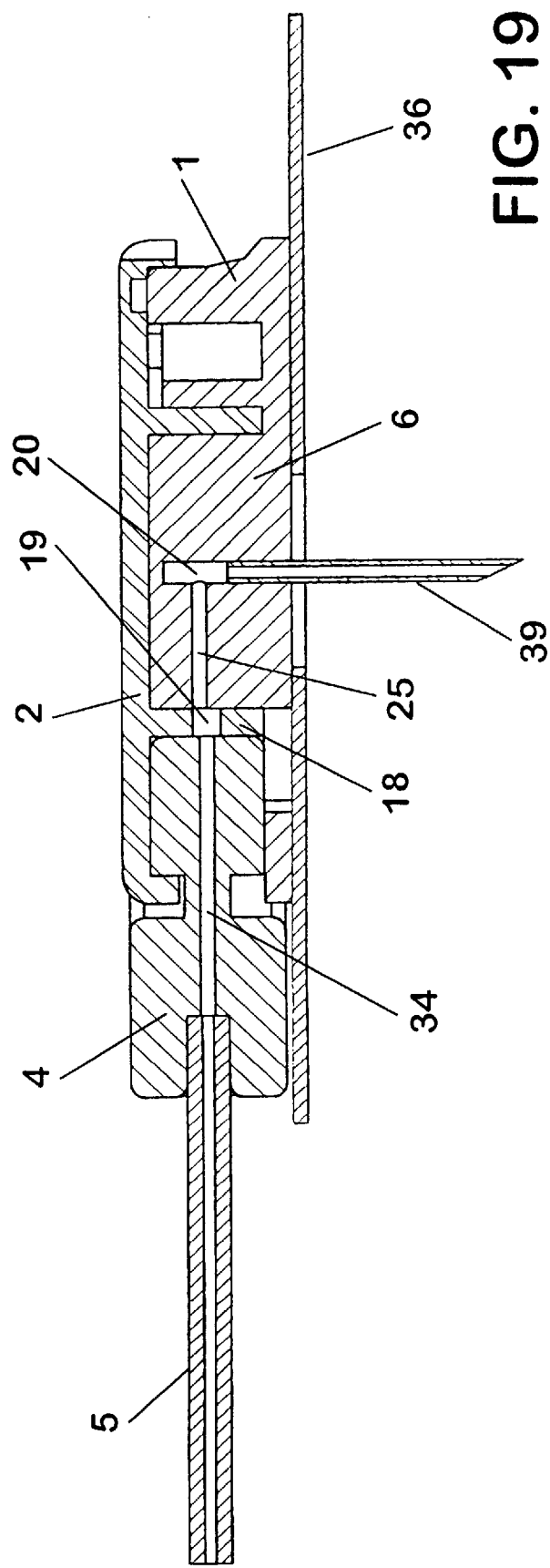

SUBCUTANEOUS INJECTION SET

BACKGROUND OF THE INVENTION

The present invention relates to injection devices for subcutaneous delivery of a medication or a therapeutic fluid by means of an external infusion system and more particularly to an injection device having releasably connected means for delivery of the medication or the therapeutic fluid from the external infusion system.

Injection devices are generally known in the art for delivering a medication or a therapeutic fluid to a subcutaneous site in a patient. Such devices commonly comprise a tubular cannula extending from a housing adapted to receive the desired medication via disconnectable means for suitable connection to further components of the infusion system. The possibility of disconnecting the injection set from the further parts of the infusion system is provided in order to improve the user comfort. The user is enabled to perform activities which do not allow the presence of a pump or the like, or which are hindered by the presence of a pump or the like. In the disconnected state only a part of the injection set is worn by the patients. This allows for increased mobility. In order to provide such disconnectable means and still maintain a fluid-tight sealing towards the interior of the housing and the tubular cannula that prevents contamination of the injection site, such devices are commonly provided with a self-sealing penetrable septum on either the housing or the disconnectable part and a hollow needle on the other part adapted to penetrate the septum. Upon withdrawal of the needle from tie septum this provides a fluid-tight sealing towards the interior of the housing. The septum and the needle further provides a fluid-tight sealing between the housing and the connector means when medication or therapeutic fluid is delivered to the patient from the external infusion system. Subcutaneous injection devices of this generally known type are known from e.g. U.S. Pat. No. 5,522,803 to Teissen-Simony and U.S. Pat. No. 5,545,143 to Fischell.

The manufacture of such device including a septum and a needle is rather cumbersome. Further The use of a septum and a needle may lead to some disadvantages during use of such device, viz. a so-called coring whereby, upon penetration of the septum, the hollow needle may become clogged by material from the septum, which may be harmful to the patient since the medication or the therapeutic fluid cannot be delivered as expected, and the potential danger of unintended needle sticks.

For these reasons there is a need for improvements in the injection devices of the type mentioned in the foregoing, and particularly with respect to providing an injection device which is far less cumbersome from a manufacturing point of view and which is not clogged by material from a septum and with respect to a device which does not need a septum and a needle to provide a fluid-tight sealing between housing and connector means in a mutually mounted position for these elements. The injection device according to the invention remedies the above mentioned disadvantages and provides further advantages which will become apparent from the following description.

SUMMARY OF THE INVENTION

The advantages of the present invention are obtained by means of an injection device comprising:

a base element having a hub with a top and a bottom and an outer surface extending between said top and said bottom, a cavity within said hub and an entry lumen extending from said outer surface to said cavity;

a top element mounted on said base element to be rotatable about an axis through said hub and having a flange with an inner surface mating with said outer surface of said hub inner the area around the entry lumen, said flange having an aperture extending between said inner surface and an outer surface, which aperture in one position of the top element in relation to the base element is aligned with said entry lumen of said hub and said flange in a further rotated position of the top element in relation to the base element covers said entry lumen in said hub;

a cannula mounted in and extending from said hub of said base element, said cannula having a lumen therethrough, said lumen communicating with the entry lumen of the central hub through said cavity;

connector means for administering a fluid to said opening in said flange of said top element.

By means of the hub of the base element and the flange of the top element which, upon mutual rotation of the top element and the base clement enables a covering of the lumen in the hub, the need for a self-sealing septum for shutting off the opening in the injection device where the medication is delivered has become eliminated. Since there is no longer a need for a septum, a needle on the means for delivering the medication or the therapeutic fluid can also be omitted. This means that the manufacturing has been significantly simplified and production costs have been decreased. The need for the elements causing the coring has been eliminated, whereby the coring problem has likewise been eliminated. The danger of unintended needle sticks is precluded.

In a preferred embodiment of the invention the top element of the injection set further comprises a flange having an inwardly facing surface directed towards the central axis of said hub and wherein said means for administering fluid to said opening in said flange comprises an outward facing surface directed away from central axis of said hub, said outwardly facing surface mating with said inward facing surface of said flange of said top clement upon rotation of said top element in relation to said base element. Hereby it is possible to releasably lock the connector means for administering the medication or the therapeutic fluid in relation to the base element and the top element. A corresponding effect could be realised if said connector means are secured in relation to said base element and said flange in the area around the aperture is provided with an increased outer diameter hereby providing a pressure against said connector means upon rotation or said top element.

In a further convenient embodiment the inwardly facing surface, the outwardly facing surface or both surfaces has/have a curvature urging the connector means for administering medication towards the inner flange of the top element upon rotation of the top element in relation to the base element. Hereby it is possible to obtain sufficient sealing between the connecting element of the connector means for administering the medication or the therapeutic fluid and the flange without any further sealing means. This desired effect can be obtained by means of off-set axis of rotation.

It is however a possibility that further sealing means are provided between the hub and the flange and/or between the flange and the means for delivering medication, in order to prevent leakage between these elements. Such sealing means are preferably O-rings or the like.

In a further preferred embodiment the subcutaneous injection set further comprises means for releasably interlocking the base element and the top element in relation to a mutually rotation about said central axis. Hereby it is ensured that the possibility of an unintended rotation of the top element in relation to the base element is eliminated, which could result in a blocking of the administering of the medication or the therapeutic fluid during use.

In a further preferred embodiment of the subcutaneous injection set means are provided for preventing a rotation of the top element in relation to the base element when the connector means for administering medication to the aperture in the flange of the top element is not present. Hereby unintended rotation of the top element in relation to the base element to a position where the aperture is aligned with the entry lumen is prevented. Such alignment could lead to a contamination of the injection set interior and the injection site. Examples of suitable means could include a biasing element forming part of the top element or a biasing element forming part of the base element which in an unloaded position blocks the rotation of tho top element in relation to the base element.

Preferably means for securing said base element in relation to the skin of a patient are provided in connection with base element. It is however possible that such means are provided as one or more separate element(s). The securing means is usually an adhesive layer.

The cannula can be either a rigid cannula or a soft cannula. The rigid cannula is usually a steel cannula although other possibilities exist. The soft cannula is usually a Teflon® cannula. It is however possible to utilise several other polymer material cannulas for this purposes.

In case said cannula is a soft cannula, there is a need for a support of this during the insertion. In this connection said cavity extends to the top of said hub and self-sealing means covering said cavity towards said top of said hub are provided. An insertion needle is provided for removable insertion through an opening in said top element, through said self-sealing means and through said cavity and said lumen of said soft cannula and extending beyond the length of said soft cannula.

In another aspect of the invention the injection set provides a fluid-tight sealing between the connector means a housing without the need of a self-sealing septum and a needle. This is obtained by an injection set comprising:

a base element having a hub with a top and a bottom and an outer surface extending between said top and said bottom, a cavity within said hub and an entry lumen extending from said outer surface to said passage;

a top element mounted on said base element to be rotatable about an axis through said hub and having a top and a bottom, where a flange extends from said bottom, said flange being provided with an aperture communicating with said entry lumen, a cannula mounted in and extending from said hub of said base element, said cannula having a lumen therethrough, said lumen communicating with the entry lumen of the central hub through said cavity;

connector means for administering a fluid to said aperture in said flange of said top element;

means for urging the connector means sealingly against the flange of the top element.

BRIEF DESCRIPTION OF THE DRAWINGS

FIG. 18 is a perspective view of an insertion needle;

FIG. 19 is a sectional view of an injection set provided with a rigid cannula;

DESCRIPTION OF THE PREFERRED EMBODIMENT

Figure 1:
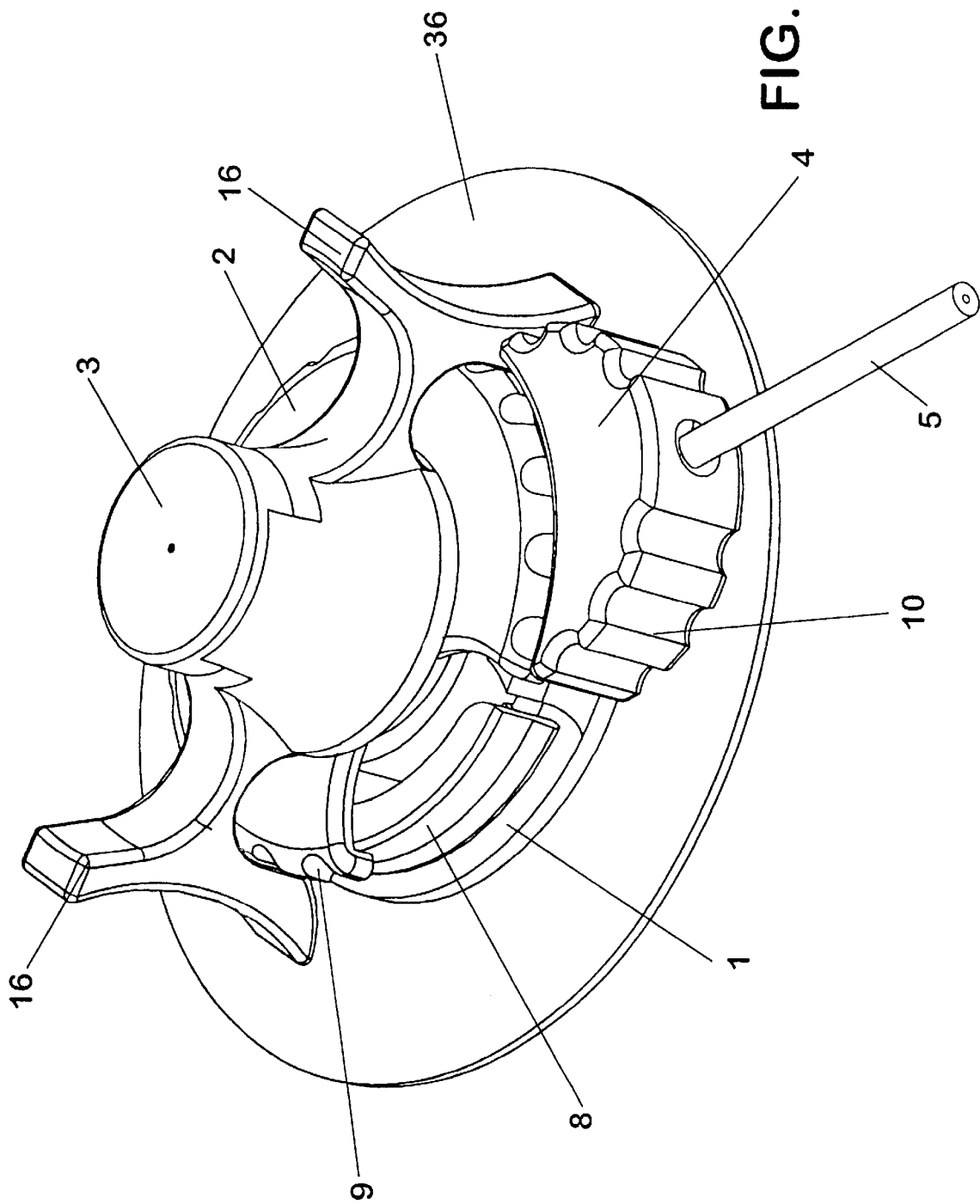
FIG. 1 is a perspective view of an injection set comprising all the features of the invention.

A preferred embodiment of the subcutaneous injection set according to the invention which is shown in FIG. 1, comprises the following elements: a base element 1, a top element 2, a needle hub 3 with an insertion needle 14 (FIG. 5) and connector means 4 comprising a hose 5 for connecting the injection set to further parts of the infusion set. The base element 1 is on the bottom side provided with an adhesive layer 36 which serves to secure the injection set to the skin of the patient during use. This configuration corresponds to the situation before and immediately after the insertion of the needle 14 and the cannula 13 into the subcutaneous fat layer of a patient. After placement the insertion needle 14 is removed and can be discarded since the primary insertion is the only use of this. On both the top element 2 and the connector 4 grooves 9 and 10 have been provided in order to improve the grip for the user hereby facilitating the rotation of the top element.

Figure 2:
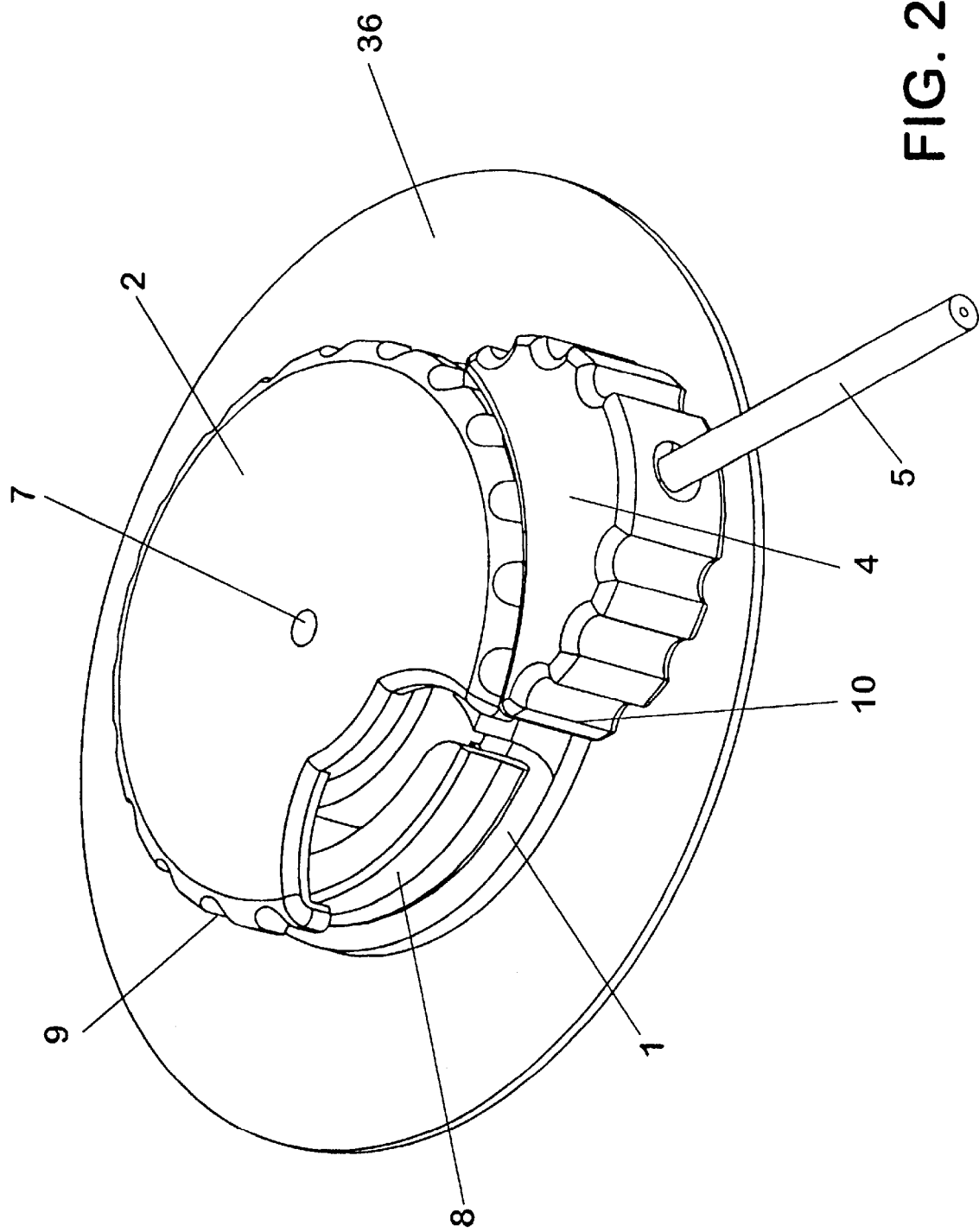
FIG. 2 is a perspective view of an injection set corresponding to FIG. 1 where the insertion needle has been removed.

From FIG. 2 the injection set appears in the configuration where the insertion needle 14 has been removed. The injection set can hereby remain on the patient for several days secured by the adhesive layer 36.

Figure 5:
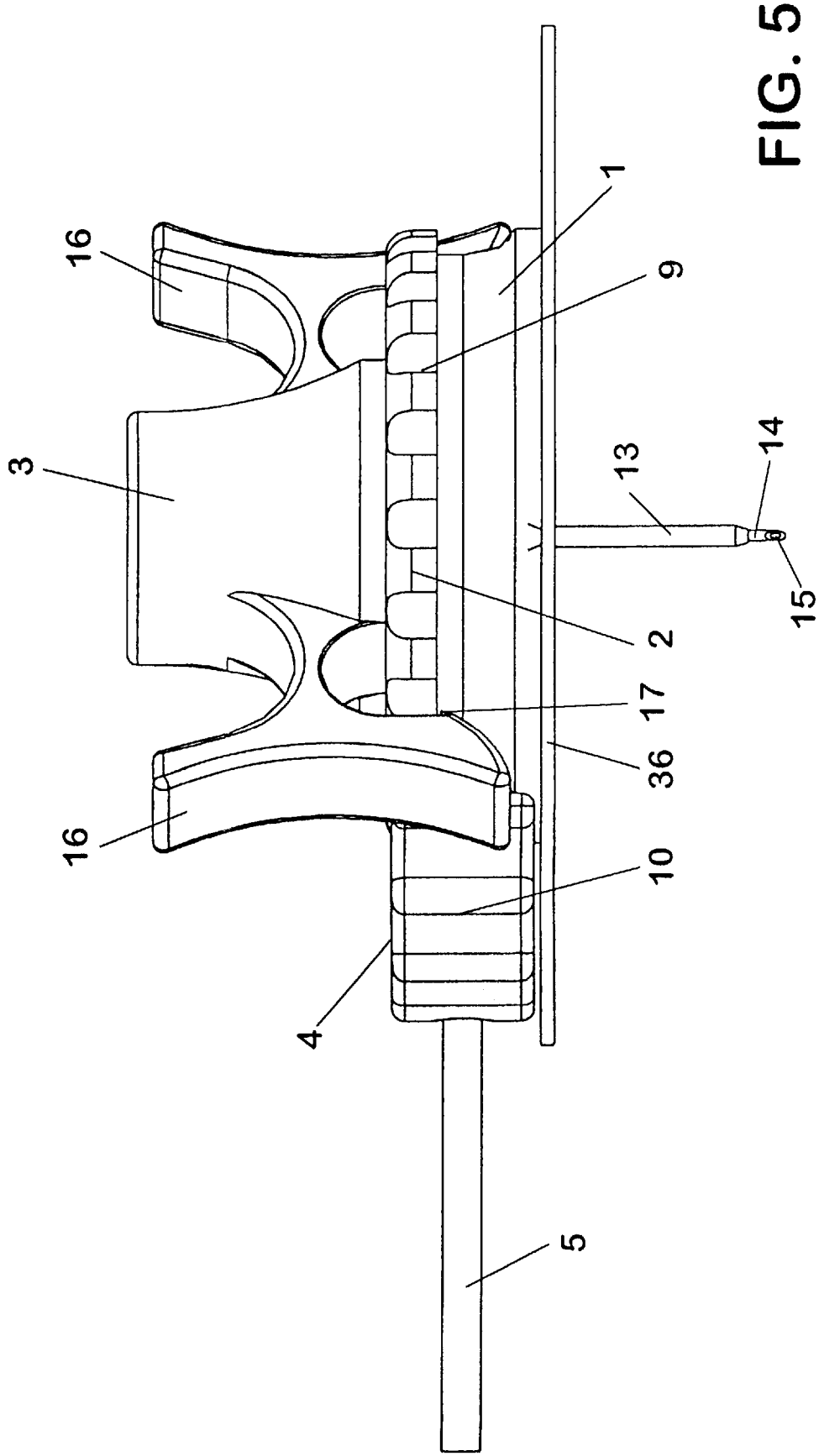
FIG. 5 is a side view of the device shown in FIG. 1.

From FIG. 5 it appears that the arms 16 of the needle hub are provided with projections 17 which interlock the needle hub 3 and the top element 2. This feature serves to secure the needle 14 against axial displacement during the insertion process. After having completed the insertion process, the needle hub 3 and the needle 14 is removed by urging the arms 16 against each other and at the same time withdrawing the needle hub 3. It appears that the needle, which is hollow, at its outer tip has an aperture 15.

Figure 3:
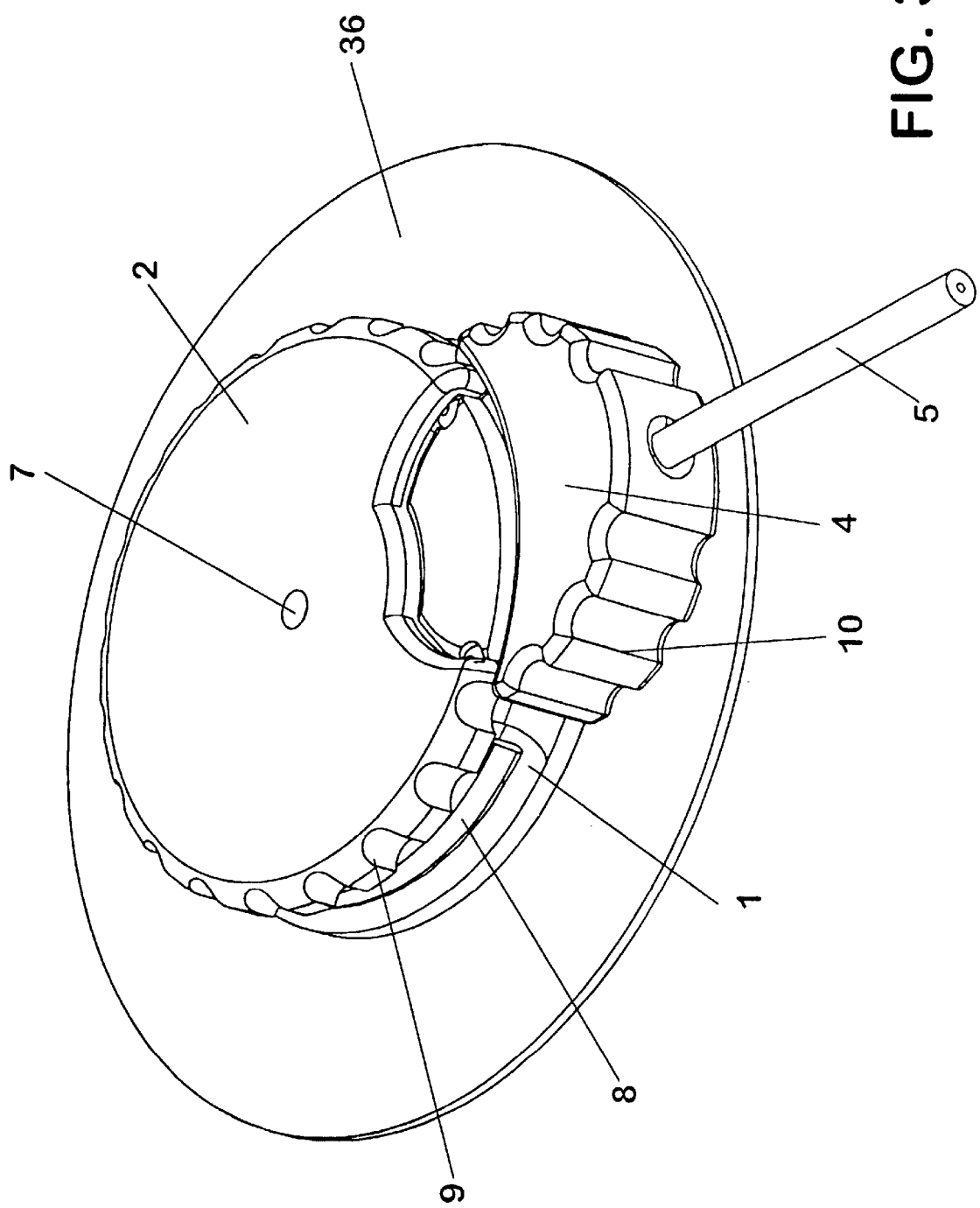
FIG. 3 is a perspective view of an injection set corresponding to FIG. 2 where the top element has been rotated to a release position.
Figure 4:
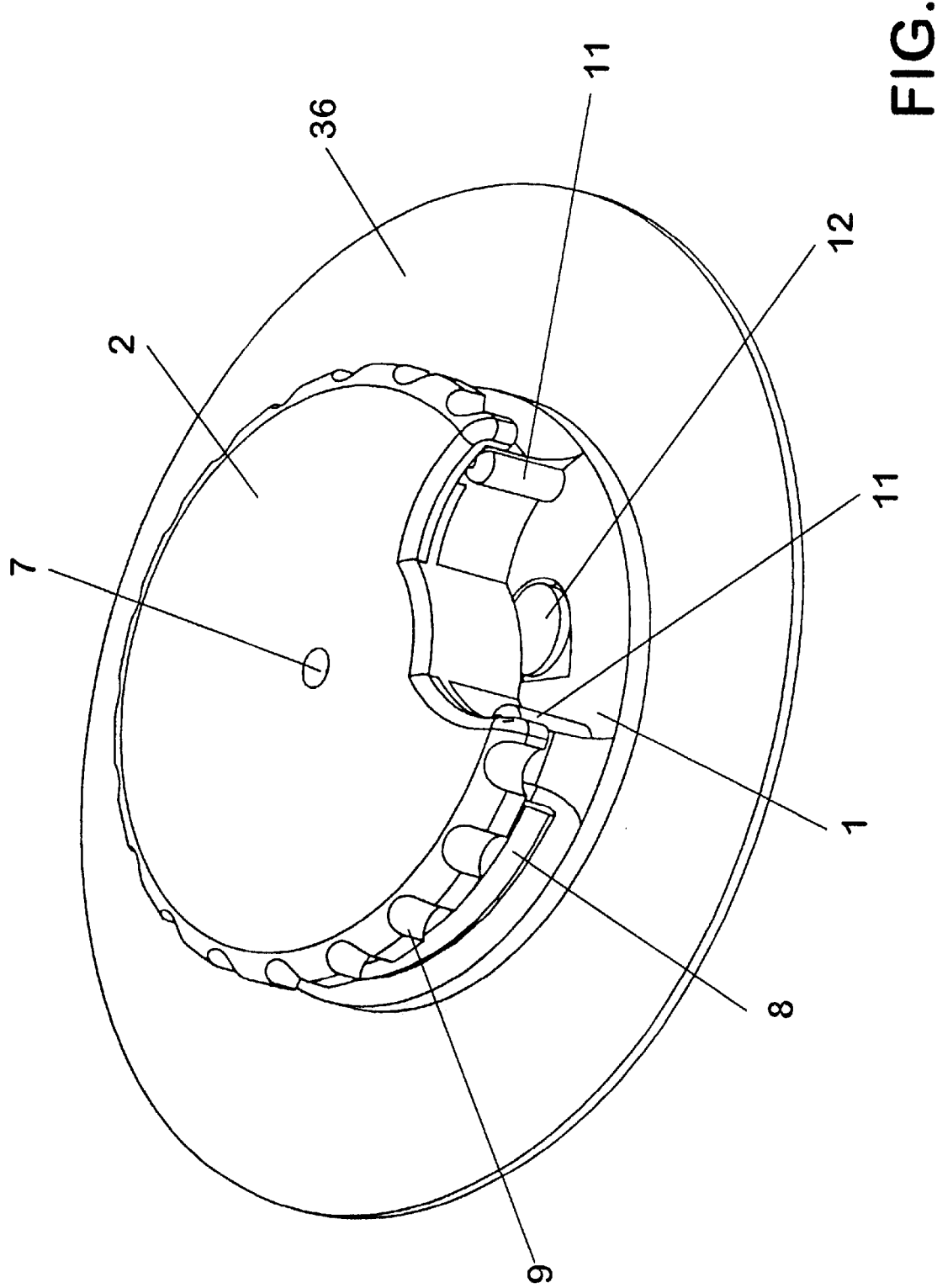
FIG. 4 is a perspective view of an injection set corresponding to FIG. 3 where the connector means has been removed.

The top element 2 is mounted to be rotatable in relation to the base element 1. The top element 2 is rotatable about a central axis which in this embodiment extends co-axially with the longitudinally axis of the insertion needle 14 and the cannula 13. The rotation can take place between two extreme positions, namely a first position where the connector means 4 are secured in relation to the top element 2 and the base element 1 us shown in FIG. 2, and a second position where the connector means 4 is releasable from the top element 2 and the base element 1, as shown in FIG. 3. In FIG. 4 the base element 1 and the top element 2 are shown where the connector means 4 has been removed from these. It appears that since projections 11 on the base element and corresponding grooves in the connector means have been provided, these projections 11 and grooves being parallel with the axis of rotation, the removal of the connector means 4 can only take place in an upward direction parallel with this axis. FIG. 4 further shows means for preventing unintended rotation of the top element in relation to the base element. These means comprise a biasing element 12 which in the unloaded state and upon an attempt to rotate the top element will abut the adjacent part of the base element 1 and thereby stop the rotation. Such rotation will lead to an opening to the injection site which could cause a contamination.

From FIG. 5 it appears that the needle 14 mounted in the needle hub 3 protrudes beyond the length of the flexible cannula 13.

Figure 6:
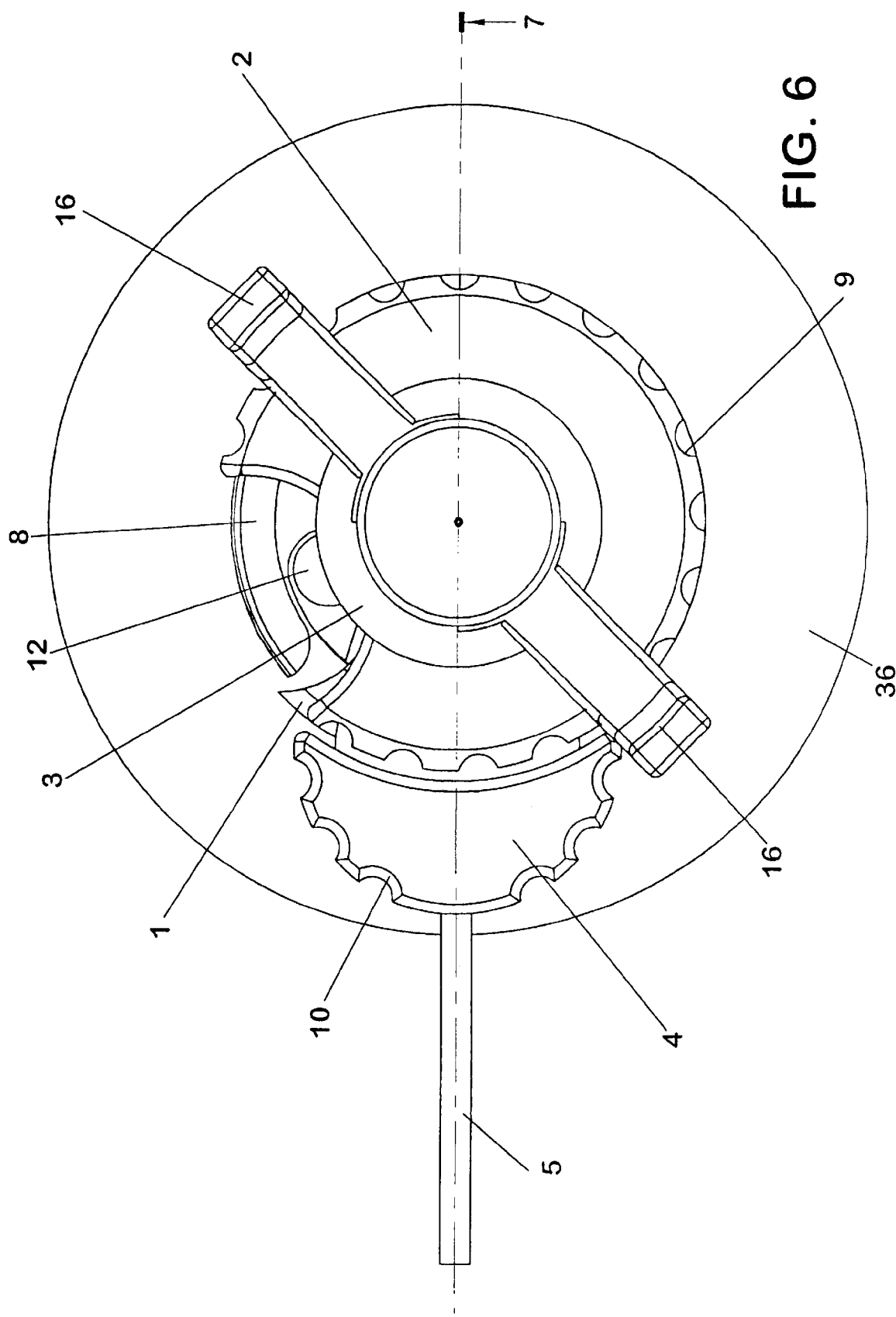
FIG. 6 is a top view of the device shown in FIG. 1.
Figure 7:
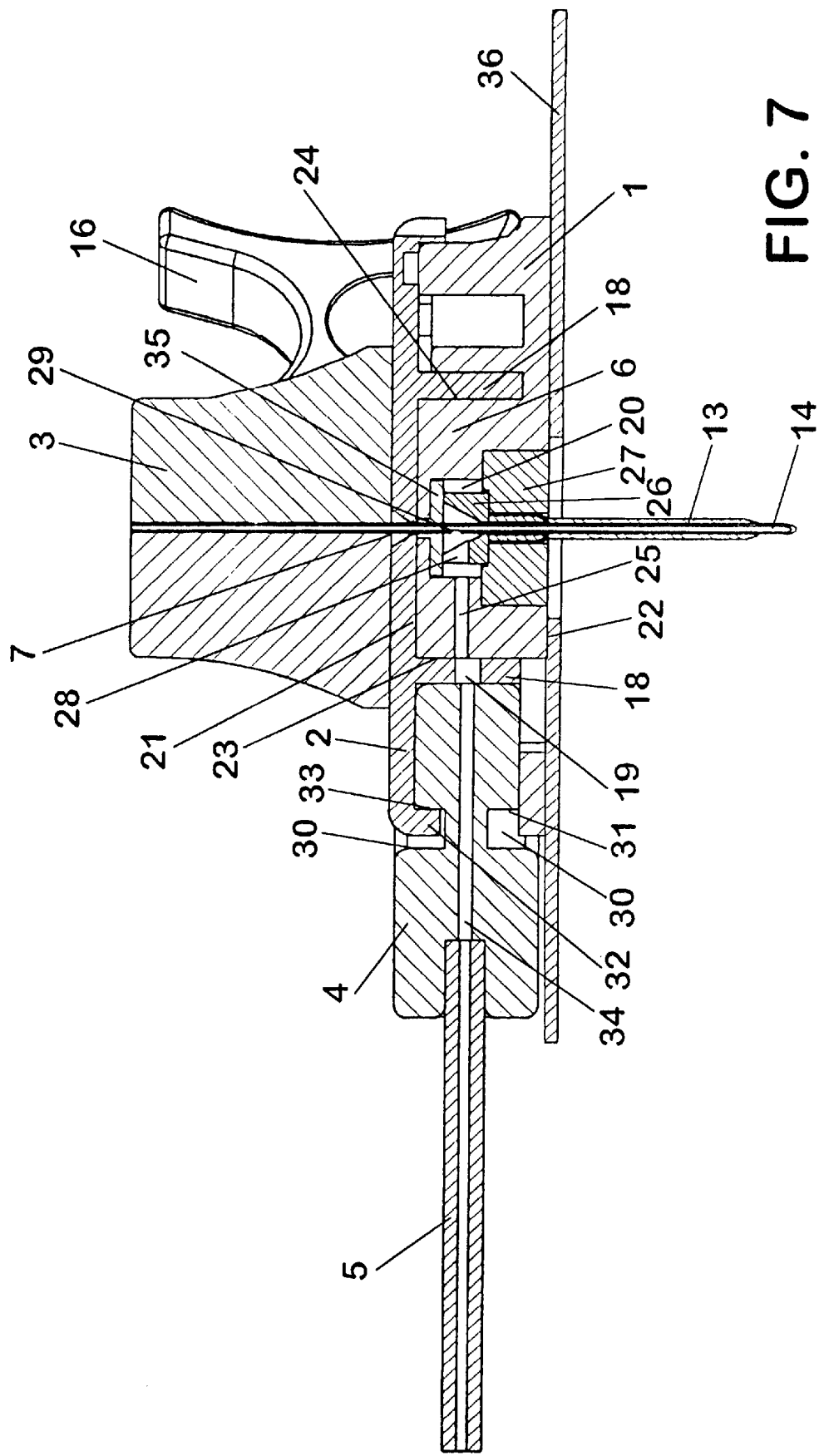
FIG. 7 is a sectional view taken along the line 7—7 in FIG. 6.

From FIG. 7 it further appears that the base element comprises a central hub 6 with a cavity 20 wherein means 26,27 for securing the soft cannula 13 are situated. Between the top 21 and the bottom 22 of this central hub 6 an outer surface 24 extends and between the cavity 20 and the outer surface 24 an entry lumen 25 is provided. The top element 2 comprises a flange 19 with an inner surface 23 which corresponds to the outer surface 24 of the hub 6. The two surfaces abuts closely to each other. Between the inner surface and the outer surface of the flange 18 an aperture 19 is provided. In one of the previously mentioned extreme positions of rotation for the top element 2 this aperture 19 is aligned with the entry lumen 25 in the hub 6, as shown in FIG. 6, whereby a fluid can be delivered from an external infusion system comprising a pump with a predetermined delivery rate through a hose 5 and a bore 34 in the connector means. In the other extreme position of rotation for the top element 2 the flange 18 is covering the entry lumen 25 and thereby blocking the delivery of fluid. From FIG. 7 the path for the insertion needle 14 becomes apparent. The needle 14 is secured in the needle hub 3. The needle 14 is inserted through a hole 7 in the top element and protrudes through a self-sealing septum 35, which separates a cavity 20 within the base element 1 from the surrounding environment, protrudes further through this cavity 20 and through the means 26,27 for securing the soft cannula 13 and through the lumen of the cannula 13 itself to a point beyond the outer tip of the soft cannula. The needle 14 hereby prepares the way for the soft cannula 13 during the insertion process. The septum is made from a usual flexible polymer material. It is apparent from the foregoing description that the septum only is penetrated once by the insertion needle.

The means as shown for securing the cannula are provided in case the cannula is of a type which can not be secured directly to the base element by e.g. gluing or welding. This is the case it the cannula is made from Teflon®. The means comprise a first element 26 inserted in the cannula and a second element 27 fitted around the cannula in the area where the first element 26 has been inserted hereby providing a firm grip around the cannula the element 27 can the be secured in relation to the base element. In the shown embodiment the element 26 abuts the septum 35 hereby supporting this.

Figure 8:
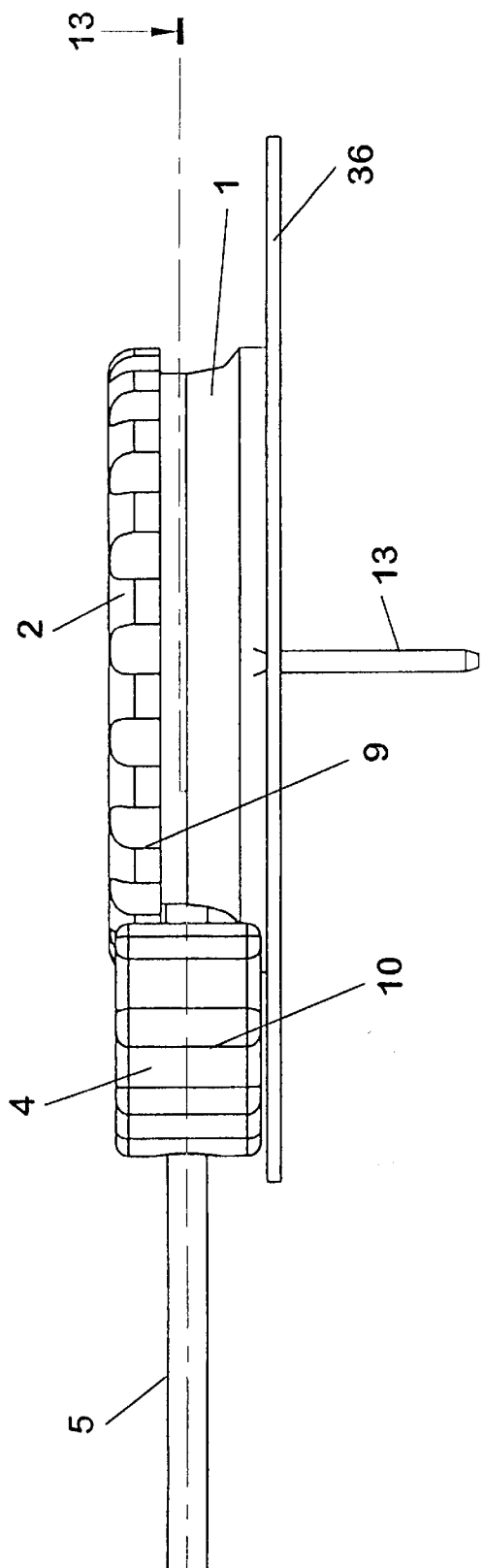
FIG. 8 is a side view of the device shown in FIG. 2.

From FIG. 8 a side view of the injection set in the normal open position for the aperture in the flange of the top element is shown.

Figure 9:
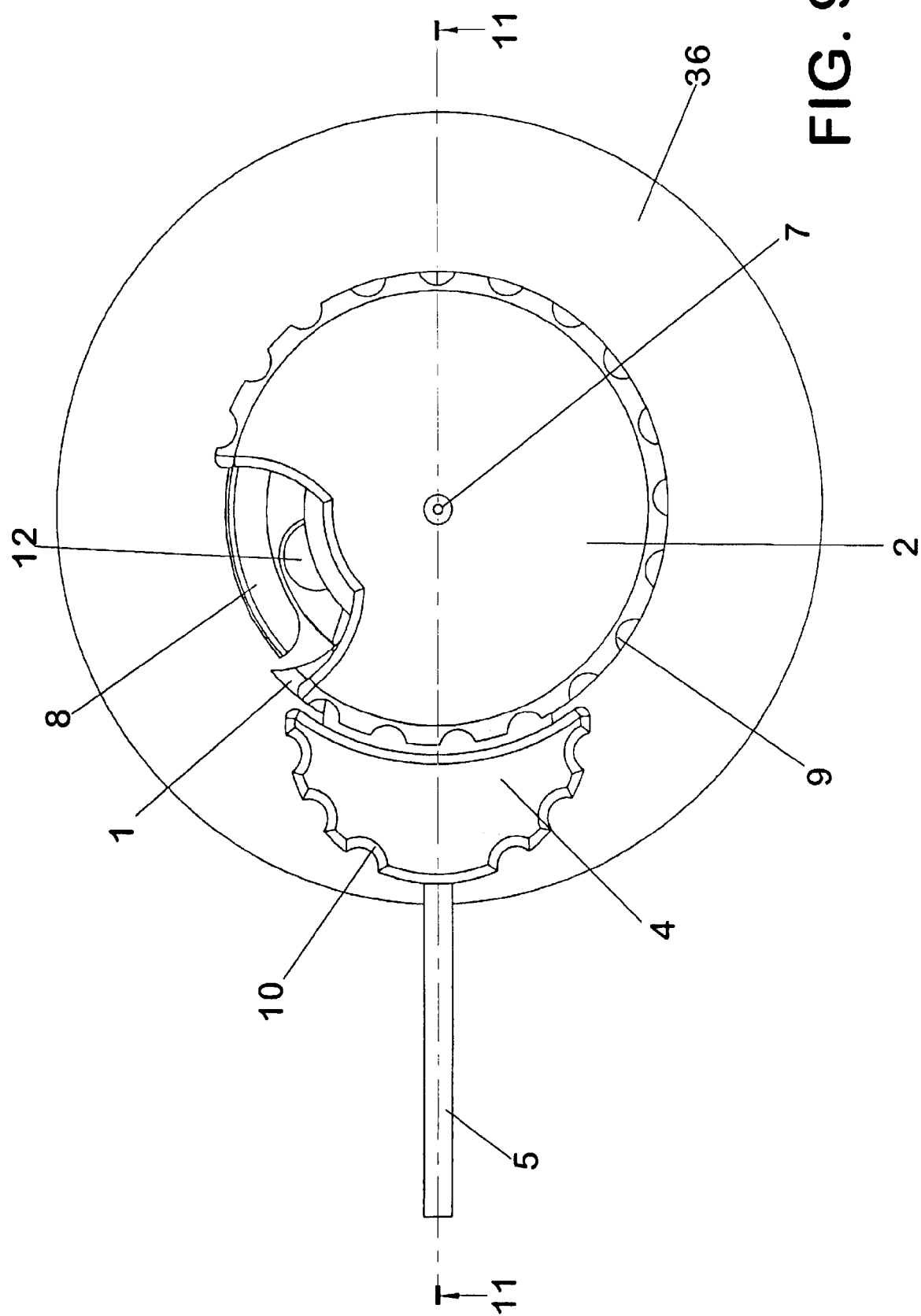
FIG. 9 is a top view of the device corresponding to FIG. 2.
Figure 10:
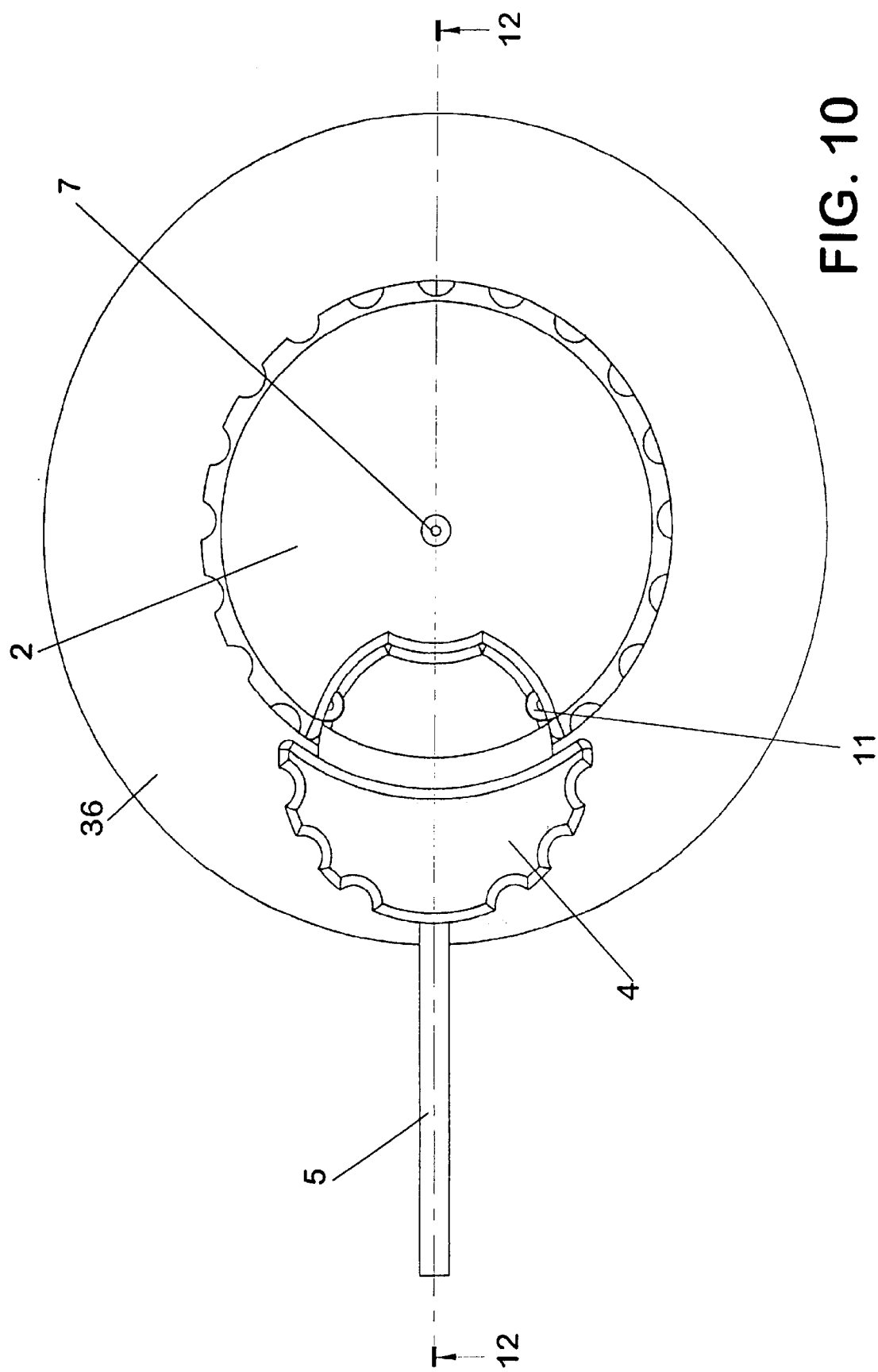
FIG. 10 is a top view corresponding to FIG. 3 where the top element has been rotated to a release position.

FIG. 9 and FIG. 10 are top views of the injection set in an open position and a closed position, respectively, for the aperture in the flange of the top element in relation to the entry lumen in the hub.

Figure 11:
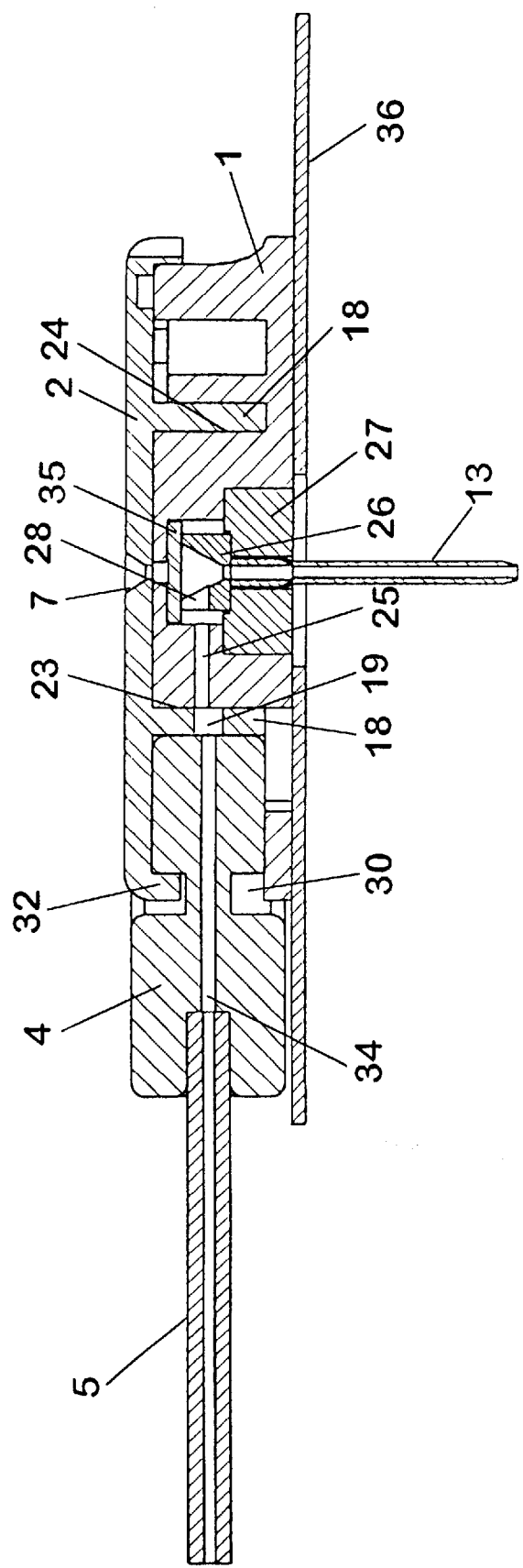
FIG. 11 is a sectional view taken along the line 11—11 in FIG. 9.
Figure 12:
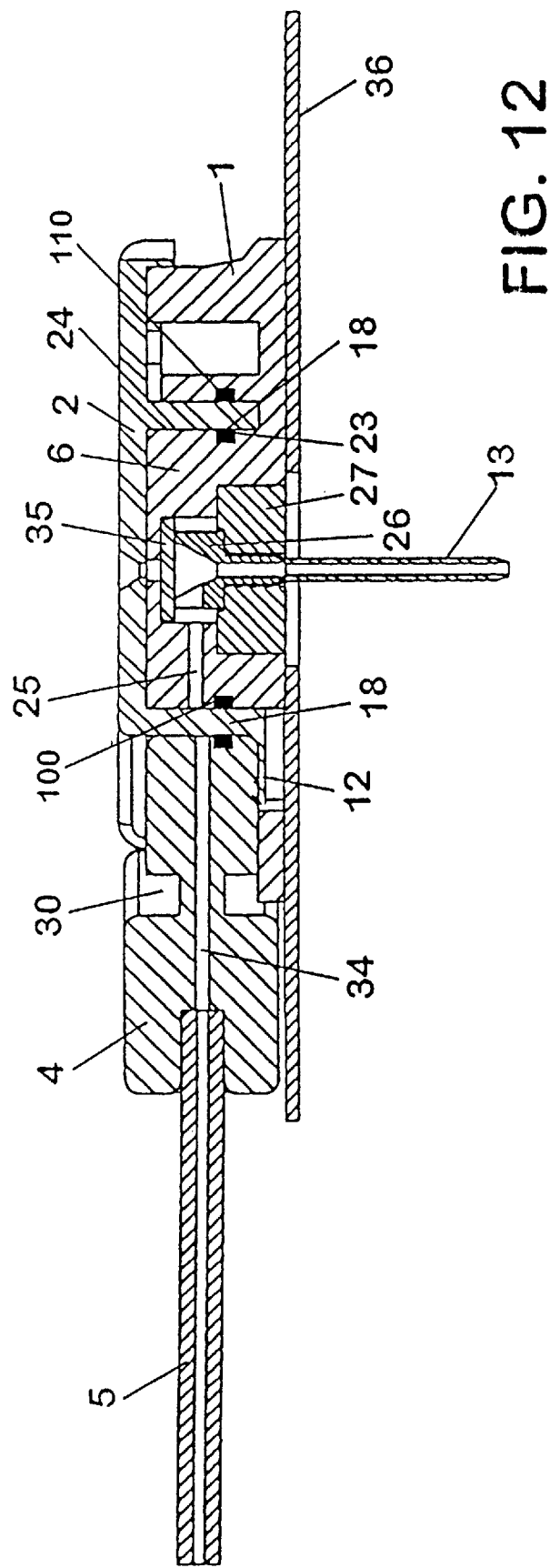
FIG. 12 is a sectional view taken along the line 12—12 in FIG. 10.

FIG. 11 and FIG. 12 are vertical sectional views of the injection set in an open position and a closed position, respectively, for the aperture 19 in the flange 18 of the top element 2 in relation to the entry lumen 25 in the hub 6. In the open position an inwardly facing surface 33 of an outer flange 32 extending downwards from the outer rim of the top element urges against an outwardly facing surface 31 of the connector means 4 hereby urging the connector means against the inner flange 18 comprising the aperture 19 which forms part of the flow path. In the closed position the connector means 4 are not influenced by the flange 32 and can therefor be removed from the base element 1 and the top element 2. Due to this urging effect upon rotation of the top element 2 towards the open position an air- and fluid-tight sealing between the connector means 4 and the inner flange 18 can be obtained. Between the inner flange 18 and the hub 6 the sealing effect is provided due to a close fitting of the outer surface 24 of the hub 6 and lie inner surface 23 of the flange 18. It is however possible to provide sealing means between the connector means and the inner flange and/or between the inner flange and the central hub. Such sealing means could comprise O-rings or the like suitable for use in connection with the medical purpose of the injection set. It appears further that the connector 4 is symmetrical about a horizontal plane which eliminates the possibility of incorrect positioning of the connector 4 in relation to the base element 1.

Figure 13:
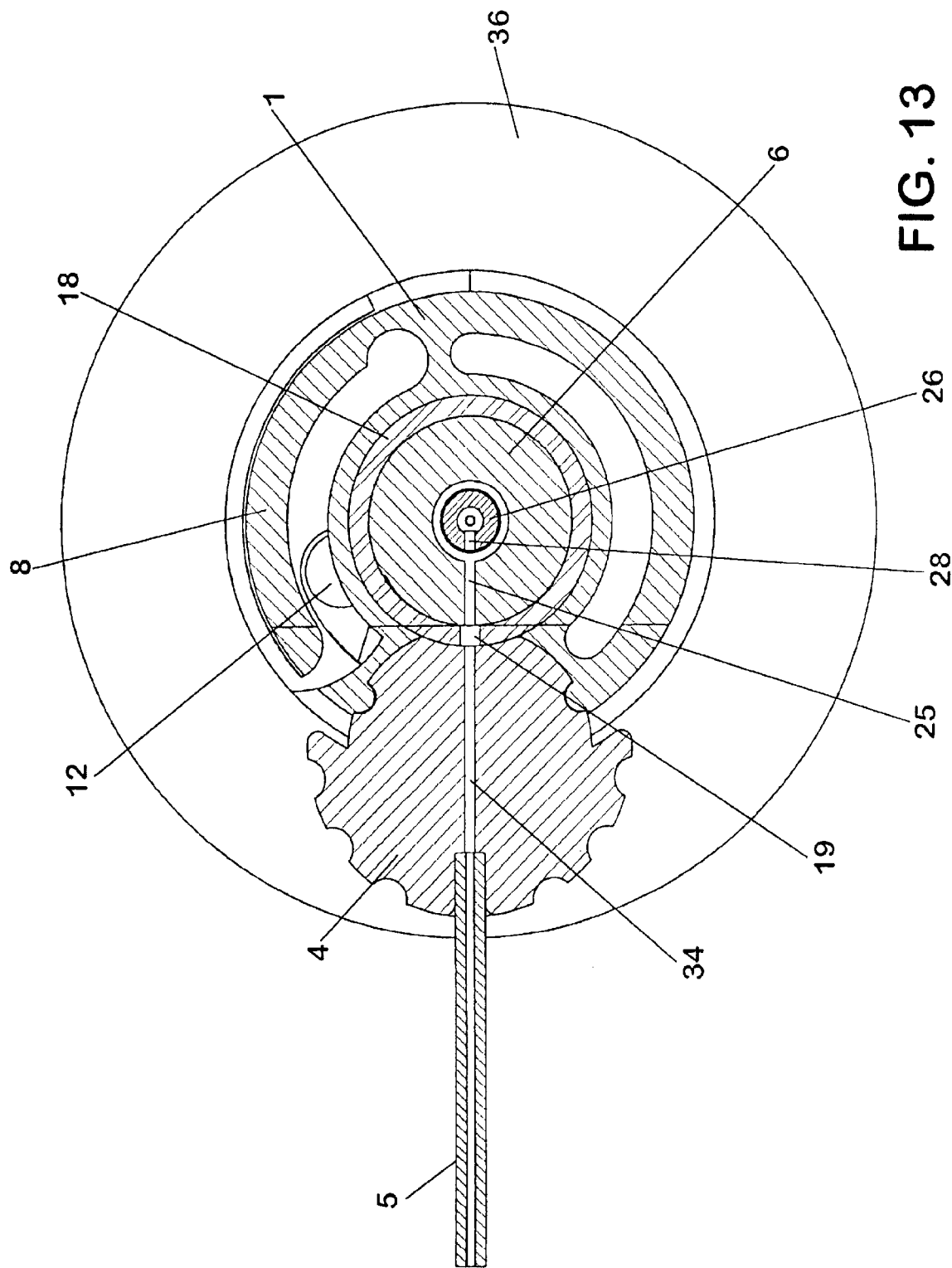
FIG. 13 is a sectional view taken along the line 13—13 in FIG. 8.
Figure 14:
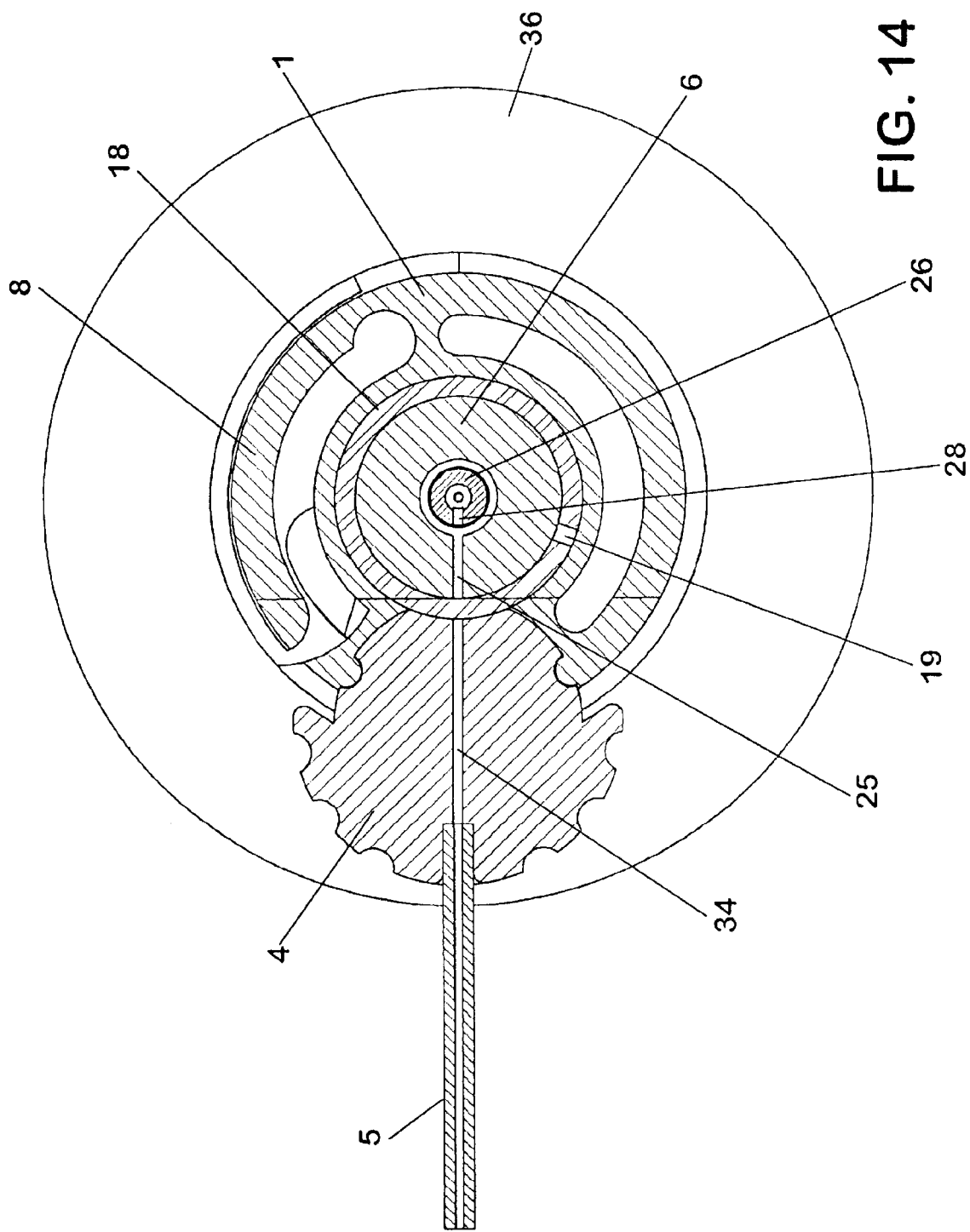
FIG. 14 is a sectional view corresponding to FIG. 11 where the top element has been rotated to a release position.

The position of the aperture 19 in the inner flange 18 of the top element 2 in the open position and the closed position becomes more apparent from the horizontal sectional views shown in FIG. 13 and FIG. 14, respectively. In FIG. 13 the flow path is shown through the hose 5, the connector 4, the aperture 19 in the flange 18, the entry lumen 25 in the hub 6 and a slit 28 in the means 26 for securing the soft cannula 13 and the cannula itself which leads the fluid to the subcutaneous injection site. In FIG. 14 the top element 2 has been rotated whereby the flange 18 covers the entry lumen 25 and thereby shuts off the flow path between the connector means 4 and the entry lumen 25. The entry lumen 25 is in this position for the top element 2 fluid-tight sealed from the environment. It appears that the connector 4 around the outlet has a surface corresponding to the outer surface of the inner flange 18. This is necessary in order to provide the above mentioned fluid-tight sealing between the connector 4 and the flange 18.

Figure 15:
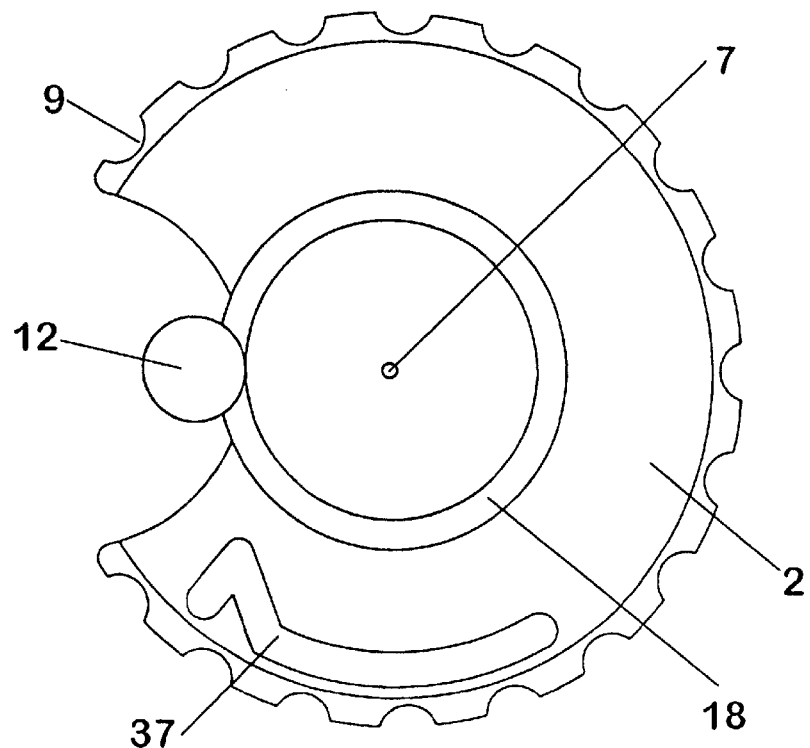
FIG. 15 is a bottom view of tho top element.
Figure 16:
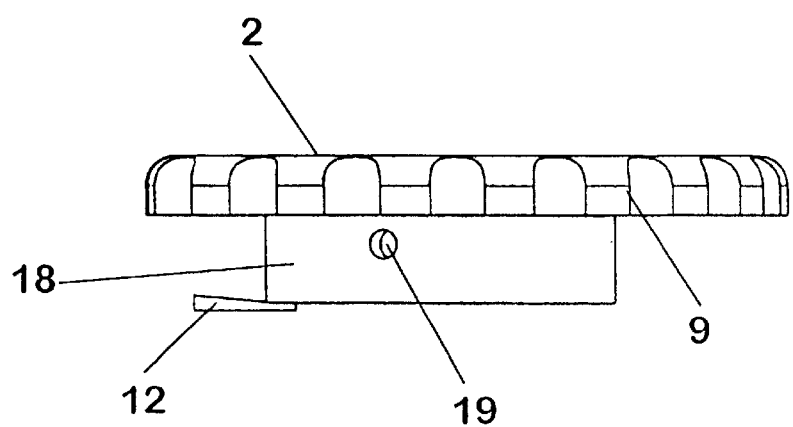
FIG. 16 is a side view of the top element.
Figure 17:
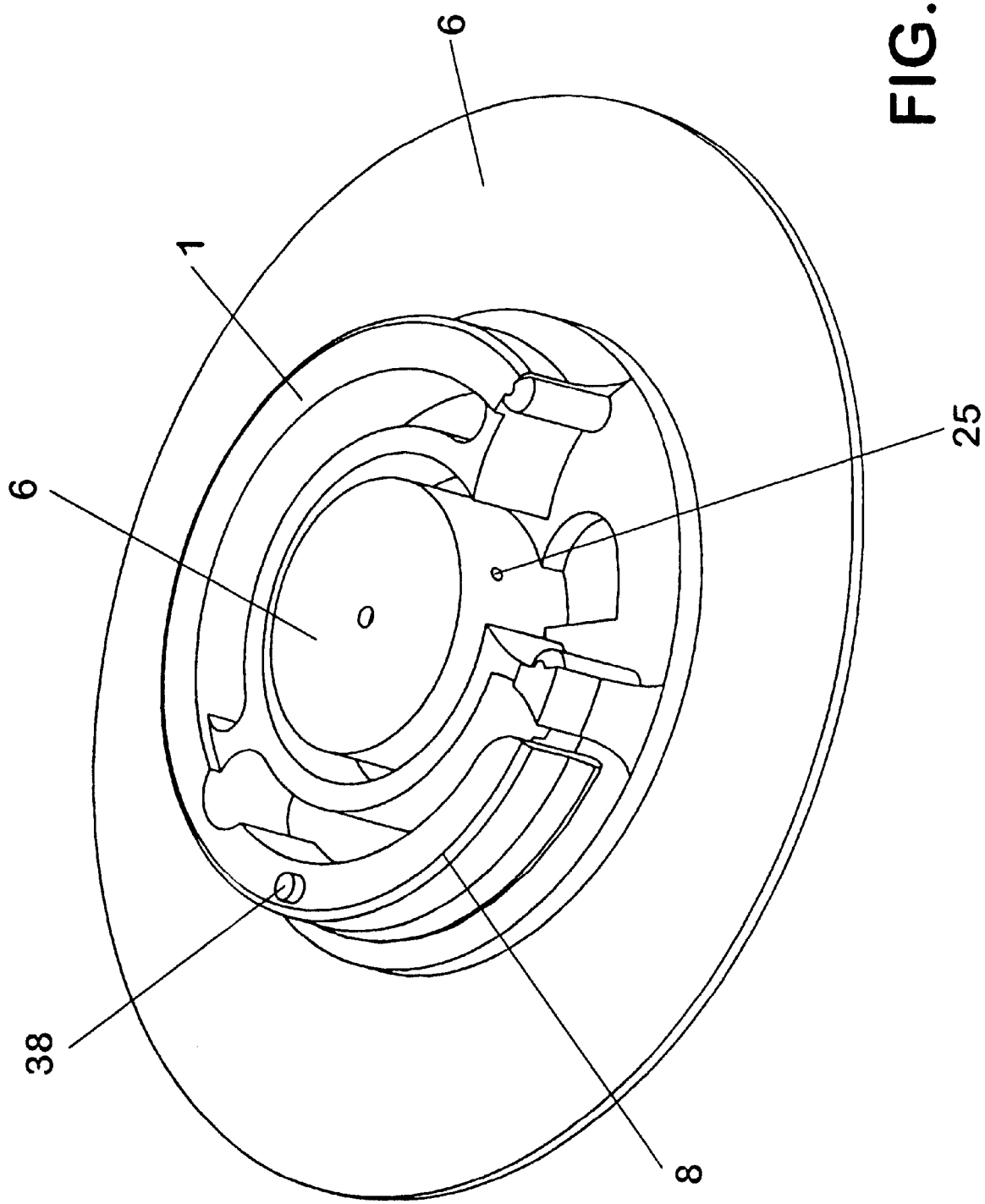
FIG. 17 is a perspective view of the base element.

From FIG. 15 it appears that a groove 37 is provided in the bottom side of the top element 2 facing the base element 1. On the top of a flexible locking arm 8 forming part of the base element 1 a knob 38 (FIG. 17) is provided which co-operates with the groove 37 in the top element 2. The groove is formed as to lock the knob 38 in the so-called open position where the aperture 19 in the flange 18 is aligned with the entry lumen 25. Hereby an unintended rotation of the top element 2 is widely precluded as a rotation will necessitate a preceding release of the knob 38 from the groove 37. The release is caused by pushing the flexible locking arm 8 towards the central part 6 of the base element 1. The rotation must be effected simultaneously with the pushing of the locking arm 8. This combined pushing and rotation impedes the unintended rotation and thereby improves the safety of the device in use.

The biasing element 12 has previously been described as to the function regarding prevention unintended rotation of the top element during absence of the connector 4. In the presence of the connector 4 and in the open position the biasing means 12 rests in an unloaded position as shown in FIG. 6. Hereby undesired fatigue which could have been caused by constant load is prevented which ensures the functionality of this feature after a long-term storing period.

The needle hub 3 and the insertion needle 14 appears from FIG. 18.

In FIG. 19 an embodiment with a rigid cannula 39, preferably a steel cannula, is shown in section. It appears that similar elements as shown ill connection with the embodiment of FIGS. 1–18 for the opening and closing of the entry lumen are present in this embodiment. The aperture 7 in the top element 2, the upper opening in the hub 1 and the septum 35 have been omitted since there is no need for an insertion needle due to the rigidity of the cannula.

What is claimed is:

1. A subcutaneous injection set comprising:
   a base element having a hub with a top, a bottom and an outer surface, said outer surface extending between said top and said bottom, a cavity within said hub and an entry lumen extending from said outer surface to said cavity;
   a top element mounted on said base element to be rotatable about an axis through said hub and having an inner flange with an outer surface and an inner surface, said inner surface of said flange mating with said outer surface of said hub in the area around the entry lumen, said flange having an aperture extending between said inner and outer surface of said flange, which aperture in one position of the top element in relation to the base element is aligned with said entry lumen of said hub and said flange in a further rotated position of the top element in relation to the base element covers said entry lumen in said hub; a cannula mounted in and extending from said hub of said base element so as to protrude from said bottom, said cannula having a lumen therethrough, said lumen communicating with the entry lumen of said hub to said cavity;
   connector means for administering a fluid to said aperture in said flange of said top element.

2. An injection set as defined in claim 1, wherein the connector means comprises an end area mating with said outer surface of said flange and where means are provided for urging said connector means against said outer surface of said flange.

3. An injection set as defined in claim 2, wherein said top element further comprises an outer flange having an inwardly facing surface directed towards the axis through said hub and wherein said connector means for administering fluid to said opening in said flange comprises an outwardly facing surface directed away from said axis through said hub, said outwardly facing surface mating with said inwardly facing surface of said outer flange of said top element upon rotation of said top element in relation to said base element.

4. A subcutaneous injection set as defined in claim 3, wherein said inwardly facing surface of said outer flange has a curvature adapted to urge the connector means for administering medication towards the inner flange of the top element.

5. An injection set as defined in claim 1, further comprising sealing means between said hub and said inner flange.

6. An injection set as defined in claim 1, further comprising sealing means between said flange and said connector means for delivering medication.

7. A subcutaneous injection set as defined in claim 1, further comprising manually operable means for releasably interlocking the base element and the top element for preventing rotation of said top element about said axis.

8. A subcutaneous injection set as defined in claim 1, further comprising rotation preventing means activatable by said connector means and adapted for preventing rotation of the top element in relation to the base element, said rotation preventing means being operable between a first position and a second rotation preventing position by said connector means and being adapted to assume said second position when the connector means for administering medication to said aperture in said inner flange of the top element is not present.

9. A subcutaneous injection set as defined in claim 8, wherein said rotation preventing means for preventing a rotation comprises a biasing element forming part of the top element.

10. An injection set as defined in claim 1, wherein means for securing said base element in relation to the skin of a patient are provided.

11. An injection set as defined in claim 1, wherein said cannula is a soft cannula, wherein said cavity extends to the top of said hub and wherein self-sealing means covering said cavity towards said top of said hub are provided, wherein an insertion needle is provided for removable insertion though an opening in said top element, through said self-sealing means and through said cavity and said lumen of said soft cannula and extending beyond the length of said soft cannula.

12. A subcutaneous injection set comprising: a base element having a hub with a top, a bottom and an outer surface, said outer surface extending between said top and said bottom, a cavity within said hub and an entry lumen extending from said outer surface to said cavity; a top element mounted on said base element to be rotatable about an axis through said hub and having a top, a bottom and an inner flange extending from said bottom, said flange being provided with an outer surface and an inner surface, said inner surface of said flange mating with said outer surface of said hub in the area around the entry lumen, said flange having an aperture extending between said inner and outer surface of said flange, which aperture in one position of the top element in relation to the base element is aligned with said entry lumen of said hub and said flange in a further rotated position of the top element in relation to the base element covers said entry lumen in said hub; a cannula mounted in and extending from said hub of said base element so as to protrude from said bottom, said cannula having a lumen therethrough, said lumen communicating with the entry lumen of said hub to said cavity; connector means for administering a fluid to said aperture in said flange of said top element; means for urging the connector means sealingly against said flange of said top element.

13. An injection set as defined in claim 12, wherein said top element further comprises an outer flange having an inwardly facing surface directed towards the axis through said hub and wherein said connector means administering fluid to said opening in said flange comprises an outwardly face surface directed away from axis through said hub, said outwardly facing surface mating with said inwardly facing surface of said outer flange of said top element upon rotation of said top element in relation to said base element.

14. A subcutaneous injection set as defined in claim 13, wherein said inwardly facing surface of said outer flange has a curvature adapted to urge the connector means for administering medication towards the inner flange of the top element.

15. A subcutaneous injection set as defined in claim 12, further comprising sealing means between said hub and said inner flange and sealing means between the flange and the means for delivering medication.

16. A subcutaneous injection set as defined in claim 12, further comprising manually operable means for releasably interlocking the base element and the top element for preventing rotation of said top element about said axis.

17. A subcutaneous injection set as defined in claim 12, further comprising rotation preventing means activatable by said connector means and adapted for preventing rotation of the top element in relation to the base element, said rotation preventing means being operable between a first position and a second, rotation preventing position by said connector means and being adapted to assume said second position when the connector means for administering medication to said aperture in said inner flange of the top element is not present.

18. A subcutaneous injection set as defined in claim 17, wherein said rotation preventing means for preventing a rotation comprises a biasing element forming part of the top element.

19. An injection set as defined in claim 12, wherein means for securing said base element in relation to the skin of a patient are provided.

20. An injection set as defined in claim 12, wherein said cannula is a soft cannula, wherein said cavity extends to the top of said hub and wherein self-sealing means covering said cavity towards said top of said hub are provided, wherein an insertion needle is provided for removable insertion through an opening in said top element, through said self-sealing means and through said cavity and said lumen of said soft cannula and extending beyond the length of said soft cannula.

21. A subcutaneous injection set comprising:
a base element having a hub with a top, a bottom and an outer surface, said outer surface extending between said top and said bottom, a cavity within said hub and an entry lumen extending from said outer surface to said cavity;
a top element mounted on said base element to be rotatable about an axis through said hub and having an inner flange with an outer surface and an inner surface, said inner surface of said flange mating with said outer surface of said hub in the area around the entry lumen, said flange having an aperture extending between said inner and outer surface of said flange, which aperture in one position of the top element in relation to the base element is aligned with said entry lumen of said hub and said flange in a further rotated position of the top element in relation to the base element covers said entry lumen in said hub; a cannula mounted in and extending from said hub of said base element so as to protrude from said bottom, said cannula having a lumen therethrough, said lumen communicating with the entry lumen of said hub to said cavity; connector means for administering a fluid to said aperture in said flange of said top element, wherein the connector means comprises an end area mating with said outer surface of said flange and where means are provided for urging the connector means against said outer surface of said flange.

22. An injection set as defined in claim 21, wherein said top element further comprises an outer flange having an inwardly facing surface directed towards the axis through said hub and wherein said connector means for administering fluid to said opening in said flange comprises an outwardly facing surface directed away from said axis through said hub, said outwardly facing surface mating with said inwardly facing surface of said outer flange of said top element upon rotation of said top element in relation to said base element.

23. A subcutaneous injection set as defined in claim 21, wherein said inwardly facing surface of said outer flange has a curvature adapted to urge the connector means for administering medication towards the inner flange of the top element.

24. An injection set as defined in claim 21, further comprising sealing means between said hub and said inner flange.

25. An injection set as defined in claim 21, further comprising sealing means between said flange and said connector means for delivering medication.

26. A subcutaneous injection set as defined in claim 21, further comprising manually operable means for releasably interlocking the base element and the top element for preventing rotation of said top element about said axis.

27. A subcutaneous injection set as defined in claim 21, further comprising rotation preventing means activatable by said connector means and adapted for preventing rotation of the top element in relation to the base element, said rotation preventing means being operable between a first position and a second; rotation preventing position by said connector means and being adapted to assume said second position when the connector means for administering medication to said aperture in said inner flange of the top element is not present.

28. A subcutaneous injection set as defined in claim 27, wherein said rotation preventing means for preventing a rotation comprises a biasing element forming part of the top element.

29. An injection set as defined in claim 21, wherein means for securing said base element in relation to the skin of a patient are provided.

30. An injection set as defined in claim 21, wherein said cannula is a soft cannula, wherein said cavity extends to the top of said hub and wherein self-sealing means covering said cavity towards said top of said hub are provided, wherein an insertion needle is provided for removable insertion through an opening in said top element, through said self-sealing means and through said cavity and said lumen of said soft cannula and extending beyond the length of said soft cannula.

\* \* \* \* \*